United States Patent [19]

Johnson

[11] 4,251,536

[45] Feb. 17, 1981

[54] RODENTICIDES COMPRISING 6-AMINONICOTINAMIDE OR 6-AMINONICOTINOHYDROXAMIC ACID

[76] Inventor: Willard J. Johnson, 14 Foothills Dr., Nepean, Ontario, Canada, K2H 6K3

[21] Appl. No.: 87,020

[22] Filed: Oct. 22, 1979

[30] Foreign Application Priority Data

Oct. 30, 1978 [CA] Canada .................................. 314772

[51] Int. Cl.$^3$ ...................... A01N 43/40; A01N 25/00
[52] U.S. Cl. ........................................ 424/266; 424/17
[58] Field of Search .................................. 424/17, 266

[56] References Cited

PUBLICATIONS

Chem. Abst.–9th Collective Index page 33760CS.

Primary Examiner—Douglas W. Robinson
Attorney, Agent, or Firm—Edward E. Pascal

[57] ABSTRACT

Anticoagulant compounds have been extensively used as rodenticides during the last 20 years. In most parts of the world rats have become resistant to anticoagulants. This circumstance seriously limits the usefulness of anticoagulant rodenticides, and gives rise to the need for a novel effective rodenticide. 6-Aminonicotinamide and 6-aminonicotinohydroxamic acid have been found to be potent rodent poisons, moreso in the rat than in the mouse. They are much less toxic to other species, such as the dog. An important feature of these compounds as rodenticides is the fact that nicotinamide is an excellent and complete antidote, even when administered after toxic symptoms have appeared. 6-Aminonicotinamide and 6-aminonicotinohydroxamic acid do not have objectionable taste or odor, and hence can be mixed with food products as edible carriers. These compounds are single-dose rodenticides in that the ingestion of only a few milligrams is fatal to a rodent, resulting in depth which occurs a few days after ingestion of the poison. Unlike the anticoagulant poisons, the mechanism of action of 6-aminonicotinamide and 6-aminonicotinohydroxamic acid is such that the development of resistance to them is virtually impossible.

7 Claims, No Drawings

RODENTICIDES COMPRISING 6-AMINONICOTINAMIDE OR 6-AMINONICOTINOHYDROXAMIC ACID

The present invention relates to novel rodenticides and a method for using the same.

The great economic waste caused by the depredations of various rodents is well known; it has been estimated that probably 10% of the world's food supply is consumed or damaged by rats. Accordingly, much effort has been expended in the development of methods and means for the destruction of rodent populations. With the introduction of the anticoagulants (warfarin) in the 1950's, it was hoped that at last a selective rat poison had arrived, since ordinary domestic animals are not particularly sensitive to it. However, the appearance of rodent resistance, throughout the world, to the anticoagulants indicates the need for a novel effective rodenticide.

It has now been discovered that 6-aminonicotinamide and 6-aminonicothinohydroxamic acid are highly lethal to rodents, particularly to rats, and are unusually effective rodenticides when mixed with a food product as an edible carrier. These compounds are ingested voluntarily by rats in sufficient quantity to cause death. Moreover, it has now been discovered that even after repeated exposure, the rat does not become "bait shy", as is the case with many materials which are toxic to rodents, and that the ingestion of only a few milligrams is fatal to a rodent.

It is an object of this invention to provide compositions which are potent rodenticides. Other objects of the invention will be apparent to one skilled in the art to which the invention pertains.

The foregoing and additional objects have been accomplished by the provision of a composition comprising a food product as an edible carrier and, as a toxic ingredient, an effective concentration of a compound selected from the group consisting of 6-aminonicotinamide, 6-aminonicotinohydroxamic and salts thereof.

The active ingredients of the composition of the present invention can be combined with any of the foods or baits normally ingested by rodents such as grain, meat, and cheese. In preparing the composition of the present invention the active ingredient may be simply mixed with food or bait which is acceptable to rodents.

The active ingredients of the present composition include 6-aminonicotinamide, 6-aminonicotinohydroxamic acid, and salts thereof.

The process of the present invention is carried out by inducing rodents to ingest the composition containing the poison. Thus, the poisoned bait is made as attractive to rodents as possible and is placed in a location to which rodents have continual access.

The essential active ingredients of the composition of the present invention can be represented by the following formulae:

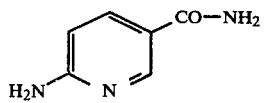

6-Aminonicotinamide

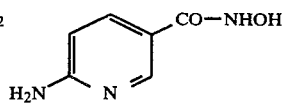

6-Aminonicotinohydroxamic acid

6-Aminonicotinamide and 6-aminonicotinohydroxamic acid seem to have no taste or odor that is detectable by the rodent, and may be used by incorporating it into a bait at a low concentration. There is a considerable delay between the ingestion of the compound and the death of the rodent, usually several days. The acute $LD_{50}$ of 6-aminonicotinamide for mice is 35 mg/kg/body wt., and for the rat 11 mg/kg/body wt. (TABLE I). Thus 6-aminonicotinamide is markedly more toxic in the rat than in the mouse. When 6-aminonicotinamide was administered to rabbits it was found to be highly toxic. However it was later found that the lethal toxicity of 6-aminonicotinamide could be nullified by administration of nicotinamide. Thus, an important advantage of 6-aminonicotinamide and 6-aminonicotinohydroxamic acid over other single-dose rodenticides resides in the fact that nicotinamide administration is an excellent antidote to their lethal toxicity.

The concurrent administration of nicotinamide in doses ranging from 12.5 to 50 mg/kg body weight has been found to provide increasingly greater protection against the lethal toxicity of 6-aminonicotinamide. This is illustrated by the experimental results shown in Table I.

TABLE I
Effect of Metabolites on the Median Lethal Dose ($LD_{50}$) of 6-AN

| Metabolite | Dose mg/kg | Species and no of animals | 6-Aminonicotinamide $LD_{50}$ (mg/kg)** | 95% Fiducial Limits |
|---|---|---|---|---|
| None | — | Mouse (30) | 35 | 33–37 |
| Nicotinamide | 12.5 | Mouse (30) | 64 | 35–77 |
| Nicotinamide | 25 | Mouse (30) | 121 | 113–129 |
| Nicotinamide | 50 | Mouse (30) | 308 | 291–331 |
| Nicotinic acid | 25 | Mouse (70) | 70 | 64–80 |
| None | — | Rat (20) | 11 | 9–13 |

*Metabolite and 6-aminonicotinamide administered i/p simultaneously. Mice: C.F.-1 strain, 18–22 gm. Rats: Sprague-Dawley, 150–160 gm. All animals were on a nutritionally adequate diet.

**$LD_{50}$ and fiducial limits calculated by the probit method from mortalities occurring over a 30-day period.

Thus, as seen in Table I, when 50 mg/kg of nicotinamide is administered concurrently with 6-aminonicotinamide the $LD_{50}$ of 6-aminoicotinamide is increased to 308 mg/kg, which is 6 times the $LD_{100}$ of 6-aminonicotinamide when given alone. The $LD_{100}$ of 6-aminonicotinamide in the mouse is 50 mg/kg. This illustrates the potent antidotal effect of nicotinamide against 6-aminonicotinamide lethality. It can also be seen in Table I that nicotinic acid gives protection against 6-aminonicotinamide, but to a lesser degree than nicotinamide.

6-Aminonicotinamide is equally effective when fed in the diet. Thus, when 6-aminonicotinamide was fed to rats at 0.025 mg per gram of diet, toxic symptoms including paralysis appear in 5 to 6 days. The addition of nicotinamide, 0.25 mg per gram of diet, to the regimen after the appearance of toxic symptoms resulted in the disappearance of the symptoms.

The effect on rats of continuous low dosage of 6-aminonicotinamide is shown in Table II. Thus, at 1 mg/kg per day, 25% of the rats were dead in 12 days, as a result of toxic effects; at 1.5 mg/kg per day 100% of the rats were dead in 12 days. The dog, on the other hand, is able to tolerate 1 mg/kg body wt. of 6-aminonicotinamide per day for a period of 14 days without developing symptoms of toxicity.

TABLE II

Cumulated Mortality of Rats Following Administration of 6-AN

| 6-AN dose mg/kg body wt/dy* | Treatment period | | | |
|---|---|---|---|---|
| | 3 days | 6 days | 9 days | 12 days |
| | Percent dead | | | |
| 0.5 | 0 | 0 | 0 | 0 |
| 1.0 | 0 | 0 | 17 | 25 |
| 1.5 | 0 | 8 | 62 | 100 |

*12 rats at each dose level.

6-Aminonicotinohydroxamic is similar to 6-aminonicotinamide in its lethal toxicity to rats. This is illustrated by the following experiment: 6-rats, each weighing 250 grams, were kept in individual cages and fed a regular rat diet. The diet was removed from the rats 12 hours prior to the beginning of the experiment (8 p.m. to 8 a.m.). At 8.00 a.m., 7 mg. of 6-aminonicotinohydroxamic acid intermixed with 5 grams of pulverized commercial rat chow was placed in a food dish in each cage. This diet was available to the rats for 3 hours, during which time all of the diet was consumed. All animals were then allowed free access to the regular diet and water ad. lib.. In 24 hours all rats showed general muscle weakness, and lack of motor control in front and hind lets. Forty-eight hours after consuming the poison, all 6 rats were prostrate. Four of the 6 rats were dead 5 days after consuming the diet containing 6-aminonicotinohydroxamic acid.

Inasmuch as 6-aminonicotinamide and 6-aminonicotinohydroxamic acid do not have an objectionable odor or taste, they are particularly suited for incorporating into edible carriers for the rodents. The latter not appear to either detect the presence of the poison or do not object to it if they do detect it. The compounds can be utilized in a variety of baits, such as ground meat, ground wheat, corn, and the like. In contrast to the anticoagulant rat poisons, the mechanism of action of these compounds is such that development of resistance to them by rodents is virtually impossible. While the invention has been described with particular reference to specific embodiments, it is to be understood that it is not to be limited thereto, but is to be construed broadly and restricted solely by the scope of the appended claims.

I claim:

1. A rodenticide including as its active ingredient a rodenticidally effective amount of 6-aminonicotinamide or an acid salt thereof, and a rodent-edible dispersion medium therefor.

2. The composition of claim 1, in which the dispersion medium is a rodent-edible food.

3. A rodenticide including as its active ingredient a rodenticidally effective amount of 6-aminonicotinohydroxamic acid or a salt thereof, and a rodent-edible dispersion medium therefor.

4. The composition of claim 3, in which the dispersion medium is a rodent-edible food.

5. A method of killing rodents comprising making available to said rodents a food bait containing a rodenticidally effective amount of 6-aminonicotinamide or an acid salt thereof, and a rodent-edible dispersion medium therefor.

6. A method of killing rodents comprising making available to said rodents a food bait containing a rodenticidally effective amount of 6-aminonicotinohydroxamic acid or a salt thereof, and a rodent-edible dispersion medium therefor.

7. A method of killing rodents as defined in claim 5 or 6, in which the dispersion medium is a rodent-edible food.

* * * * *